United States Patent
Clerc et al.

(10) Patent No.: US 9,937,676 B2
(45) Date of Patent: Apr. 10, 2018

(54) METHOD FOR CREATING A VIEWING SCREEN HAVING AN INJECTION OVERMOLDED INSERT

(71) Applicant: BNL Eurolens, Bellegarde sur Valserine (FR)

(72) Inventors: Didier Clerc, Eloise (FR); Sebastien Martins, Apremont (FR); Franck Ledien, Echallon (FR)

(73) Assignee: BNL Eurolens, Bellegarde sur Valserine (FR)

( * ) Notice: Subject to any disclaimer, the term of this patent is extended or adjusted under 35 U.S.C. 154(b) by 689 days.

(21) Appl. No.: 14/383,229

(22) PCT Filed: Mar. 7, 2013

(86) PCT No.: PCT/EP2013/054666
§ 371 (c)(1),
(2) Date: Sep. 5, 2014

(87) PCT Pub. No.: WO2013/132037
PCT Pub. Date: Sep. 12, 2013

(65) Prior Publication Data
US 2015/0029586 A1    Jan. 29, 2015

(30) Foreign Application Priority Data
Mar. 8, 2012 (FR) ..................... 12 00709

(51) Int. Cl.
*B29D 11/00* (2006.01)
*B29C 45/14* (2006.01)
(Continued)

(52) U.S. Cl.
CPC ........ *B29D 11/00807* (2013.01); *A61F 9/022* (2013.01); *B29C 45/0025* (2013.01);
(Continued)

(58) Field of Classification Search
CPC ............... B29C 45/14; B29C 45/0055; B29C 45/14065; B29D 11/00644; B29D 11/0073; A61F 9/022; G02B 5/3033; G02B 5/305
(Continued)

(56) References Cited

U.S. PATENT DOCUMENTS 5,149,183 A   9/1992  Perrott et al.
5,413,971 A   5/1995  McPherson
(Continued)

FOREIGN PATENT DOCUMENTS

EP   0 940 244 A2   9/1999
EP   1 193 044 A2   4/2002
(Continued)

OTHER PUBLICATIONS

Supplemental Amendment and Response for U.S. Appl. No. 15/012,241, filed Jul. 21, 2016; 14 pages.
(Continued)

*Primary Examiner* — Ricky D Shafer
(74) *Attorney, Agent, or Firm* — Daly, Crowley, Mofford & Durkee, LLP

(57) ABSTRACT

The invention relates to a method for creating a viewing screen (3) having an injection overmolded insert (9). Said method includes the steps of: placing an insert (9), to be overmolded, into an injection mold (1); holding the insert (9) by at least one suction nozzle (21) built into the injection mold (1); injecting, into the mold (1), a thermoplastic material for forming a mechanical substrate layer for the viewing screen; and removing the thus-formed viewing screen (3) from the mold.

10 Claims, 2 Drawing Sheets

Figure 1:
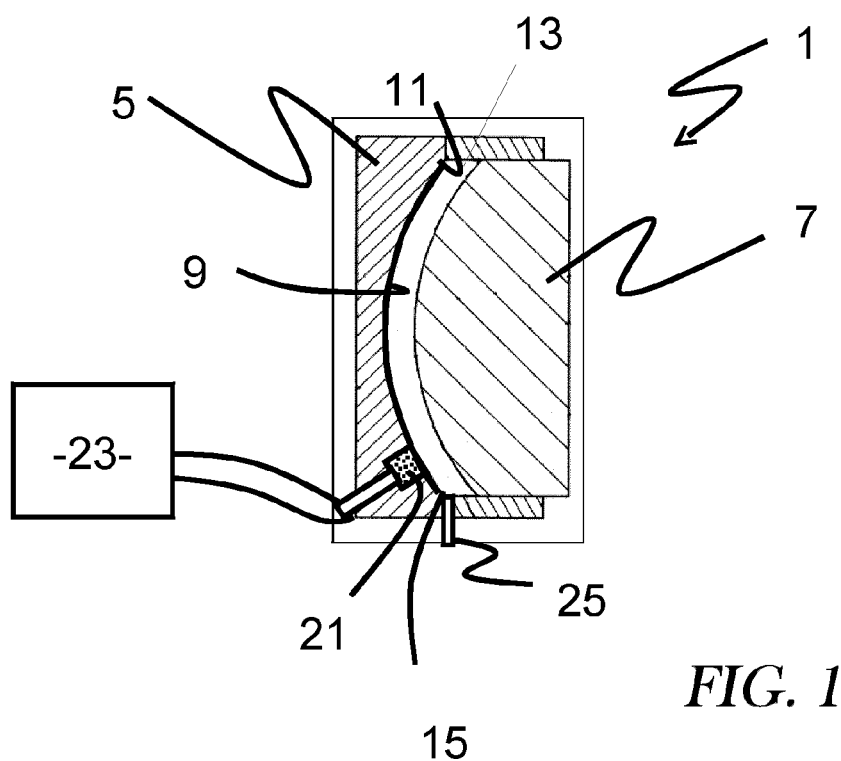

(51) Int. Cl.
| | |
|---|---|
| *B29C 45/27* | (2006.01) |
| *B29C 45/00* | (2006.01) |
| *A61F 9/02* | (2006.01) |
| *G02B 5/30* | (2006.01) |
| *B29L 11/00* | (2006.01) |
| *G02C 7/12* | (2006.01) |
| *A42B 3/22* | (2006.01) |
| *B29K 101/12* | (2006.01) |

(52) U.S. Cl.
 CPC ......... *B29C 45/0055* (2013.01); *B29C 45/14* (2013.01); *B29C 45/14065* (2013.01); *B29C 45/2708* (2013.01); *B29D 11/0073* (2013.01); *B29D 11/00644* (2013.01); *G02B 5/305* (2013.01); *A42B 3/22* (2013.01); *B29C 2045/0027* (2013.01); *B29C 2045/0058* (2013.01); *B29C 2045/14155* (2013.01); *B29K 2101/12* (2013.01); *B29K 2995/0034* (2013.01); *B29L 2011/00* (2013.01); *B29L 2011/0066* (2013.01); *G02C 7/12* (2013.01)

(58) Field of Classification Search
 USPC .................................................. 359/487.01
 See application file for complete search history.

(56) References Cited

U.S. PATENT DOCUMENTS

| | | | | |
|---|---|---|---|---|
| 5,434,707 | A * | 7/1995 | Dalzell | B29D 11/0073 264/1.32 |
| 5,922,246 | A | 7/1999 | Matsushita et al. | |
| 6,328,446 | B1 | 12/2001 | Bhalakia et al. | |
| 6,334,680 | B1 | 1/2002 | Larson | |
| 6,650,473 | B2 * | 11/2003 | Nakagoshi | B29C 45/14 264/1.32 |
| 6,807,006 | B2 * | 10/2004 | Nakagoshi | B29C 45/14 264/1.32 |
| 8,012,386 | B2 | 9/2011 | Clerc | |
| 8,733,929 | B2 | 5/2014 | Chiou et al. | |
| 9,229,247 | B2 | 1/2016 | Clerc et al. | |
| 2002/0044352 | A1 | 4/2002 | Yamamoto et al. | |
| 2003/0052423 | A1 | 3/2003 | Gross et al. | |
| 2003/0184863 | A1 | 10/2003 | Nakagoshi | |
| 2004/0223221 | A1 | 11/2004 | Sugimura et al. | |
| 2007/0076166 | A1 | 4/2007 | Kobuchi et al. | |
| 2008/0231795 | A1 | 9/2008 | Cartier | |
| 2010/0149483 | A1 | 6/2010 | Chiavetta, III | |
| 2011/0063569 | A1 | 3/2011 | Miyoshi | |
| 2011/0141432 | A1 | 6/2011 | Nesty | |
| 2014/0233105 | A1 | 8/2014 | Schmeder et al. | |
| 2014/0334000 | A1 | 11/2014 | Clerc et al. | |
| 2015/0160479 | A1 | 6/2015 | Ohkubo et al. | |
| 2016/0041408 | A1 | 2/2016 | Carlson et al. | |

FOREIGN PATENT DOCUMENTS

| | | | |
|---|---|---|---|
| EP | 1 607 203 | A1 | 12/2005 |
| EP | 1 804 088 | A2 | 7/2007 |
| EP | 2 602 655 | A1 | 6/2013 |
| FR | 2 990 774 | | 11/2013 |
| WO | WO 2004/059370 | A2 | 7/2004 |

OTHER PUBLICATIONS

Amendment and Request for Continued Examination dated Aug. 17, 2016 for U.S. Appl. No. 14/342,927; 14 pages.
U.S. Appl. No. 15/012,241, filed Feb. 1, 2016, Martins, et al.
Office Action dated Jan. 6, 2016 for U.S. Appl. No. 14/342,927; 13 pages.
Notice of Allowance dated Oct. 5, 2015 for U.S. Appl. NO. 14/383,232; 12 pages.
Amendment Under 37 C.F.R. §1.312 filed Dec. 3, 2015 for U.S. Appl. No. 14/383,232; 10 pages.
PCT International Search Report of the ISA for PCT/EP2012/067231 with English Language Translation dated Oct. 23, 2012; 6 pages.
PCT Translation of Written Opinion of the ISA for PCT/EP2012/067231 dated Oct. 23, 2012; 7 pages.
PCT Translation of Written Opinion of the ISA for PCT/EP2013/054666 dated Jun. 3, 2013; 8 pages.
PCT International Search Report and Written Opinion of the ISA dated Jun. 5, 2013 for PCT/EP2013/054663; 8 pages.
Response dated May 5, 2016 to Office Action dated Jan. 6, 2016; for U.S. Appl. No. 14/342,927; 15 pages.
Amendment and Response to Final office Action dated Oct. 19, 2016 for U.S. Appl. No. 15/012,241 as filed on Dec. 16, 2016; 12 pages.
Office Action for U.S. Appl. No. 14/342,927 dated Jan. 4, 2017; 21 pages.
Final Office Action dated Oct. 19, 2016 for U.S. Appl. No. 15/012,241; 18 pages.
International Standard; ISO 12312-1; Eye and Face Protection—Sunglasses and Related Eyewear; Part 1—Sunglasses for General Use; ISO 12312-1:2013(E); First Edition; Aug. 2013; Web. Apr. 20, 2016; 4 pages.
Chinese Office Action with English Translations of Chinese Appl. No. 201280054459.9 dated Oct. 30, 2015 and claims as allowed by CPO; 13 pages.
Office Action dated May 3, 2016 for U.S. Appl. No. 15/012,241; 18 pages.
PCT International Search Report of the ISA for PCT/EP2013/054666 dated Jun. 3, 2013; 5 pages.
Office Action dated Jun. 17, 2016 for U.S. Appl. No. 14/342,927; 22 pages.
Office Action dated Jul. 27, 2017 for U.S. Appl. No. 15/012,241; 21 pages.
Response to Office Action dated Jul. 27, 2017 from U.S. Appl. No. 15/012,241, filed Nov. 10, 2017; 13 Pages.
Appeal Brief from U.S. Appl. No. 14/342,927, filed Oct. 3, 2017; 33 Pages.

* cited by examiner

METHOD FOR CREATING A VIEWING SCREEN HAVING AN INJECTION OVERMOLDED INSERT

CROSS REFERENCE TO RELATED APPLICATIONS

This application is a U.S. National Stage application of PCT/EP2013/054666, filed in the French language on Mar. 7, 2013, and entitled "METHOD FOR CREATING A VIEWING SCREEN HAVING AN INJECTION OVERMOLDED INSERT," which claims priority to French application FR1200709 filed Mar. 8, 2012 which is incorporated herein by reference.

The present invention relates to a method for producing a viewing screen with an injection-overmolded insert, particularly for a polarizing viewing screen, to a viewing screen obtained by said method and to a mold for carrying out the method.

More specifically, viewing screens with injection-overmolded insert, notably polarizing screens obtained using the method of the invention, can be used on a mount or a frame to form a mask for example for participating in certain sports such as skiing, for night driving, for a motorcycle helmet or for protective goggles.

Polarizing masks incorporating a polarizing filter are very widespread and used for example in all activities performed in places, such as at sea or on expanses of snow, comprising zones in which light is strongly reflected. This is because these strong reflections can impair vision and in some cases cause dazzling. Masks are also highly beneficial for driving vehicles because they make it possible to limit or even eliminate parasitic reflections perceived on windshields.

In these masks, use is made of a polarizing filter, generally produced in the form of a film of polyvinyl alcohol (or PVA) polymer. Such polarizing films are conventionally obtained by incorporating molecules of dichroic pigments and/or dichroic iodine crystals into a film based on polyvinyl alcohol polymer, then by stretching the film uniaxially in order to orientate the molecules of dichroic pigments and/or the dichroic iodine crystals in the direction of stretching. A dichroic pigment means a species that may be of molecular or crystalline nature and selectively absorbs visible electromagnetic radiation for a specific spatial orientation. The polarizing films thus obtained are inexpensive and have an optical quality compatible with numerous applications, notably ophthalmic applications.

The film of PVA is then covered with one or more layers of protective material to form an insert that will be overmolded in a mold by injecting, for example, a thermoplastics material such as a polycarbonate (PC) or polyamide (PA) (such as nylon) for example.

Thus, inserts made up of CTA-PVA-CTA (CTA standing for cellulose triacetate), PC-PVA-PC, CTA-PVA-PC, CTA-PVA-PA are known, the first layer of the insert being the layer intended to be furthest away from the eye when the mask is being worn and the third layer being the one intended to be closest to the eye of the user.

To date, for manufacture, the insert is placed in the mold and held in place mechanically at four ends via the periphery.

Document EP 0940244 discloses a method of manufacturing lenses in which several suction nozzles are used to hold an insert, these nozzles being distributed all around the finished product.

However, it has been found that the holding system is difficult to set up and may, during injection overmolding, give rise to tension within the insert and this tension has an impact on the optical quality of the viewing screen.

It is one object of the invention to provide a method for producing a viewing screen with an overmolded insert that at least partially alleviates the abovementioned disadvantages.

To that end there is provided a method for producing a viewing screen having an injection-overmolded insert, comprising the steps of:
 placing an insert that is to be overmolded in an injection mold,
 holding the insert using at least one suction nozzle incorporated into the injection mold,
 injecting a thermoplastics material into the mold to form a mechanical support layer supporting the viewing screen,
 demolding the viewing screen thus formed, characterized in that the mold has only one suction nozzle positioned in a zone which, insofar as the viewing screen is concerned, corresponds to the cutout portion that accommodates the nose of a user.

According to one aspect, the suction nozzle comprises a low-porosity metal insert preventing the injected thermoplastics material from being sucked up and which is incorporated into the concave part of the injection mold.

The suction nozzle may have a transverse diameter of between 7 mm and 10 mm, preferably of 9 mm.

The metal insert of the suction nozzle may have a porosity of below 200 μm.

Typically, the suction is between 0.02 and 0.085 MPa.

According to another aspect, the insert has a size smaller than that of the finished viewing screen.

An injection nozzle for injecting the thermoplastics material is positioned edge-on in relation to the insert, near the suction nozzle and centered relative to the latter.

The overmolding thermoplastics material may be polycarbonate or polyamide.

The insert may be forced of three layers, the intermediate layer being made of polyvinyl alcohol (PVA) polymer and one or both of the two outer layers being made up of cellulose triacetate, polycarbonate or polyamide.

Another subject of the invention is a viewing screen obtained using the method as defined hereinabove, comprising, in succession, a mechanical support layer comprising a thermoplastics material forming a rear face of the viewing screen, an intermediate layer made of polyvinyl alcohol polymer, and an outer layer made of thermoplastics material forming a front face of the viewing screen.

A further subject of the invention is an injection mold for molding a viewing screen with an overmolded insert, comprising a concave part and a convex part, characterized in that the concave part has, in its part which, insofar as the viewing screen is concerned, corresponds to the cutout portion that accommodates the nose of the user, a suction nozzle for holding an insert in place.

The thermoplastics-material injection nozzle is, for example, positioned edge-on in relation to the insert, near the suction nozzle and centered with respect to the latter.

Figure 2:
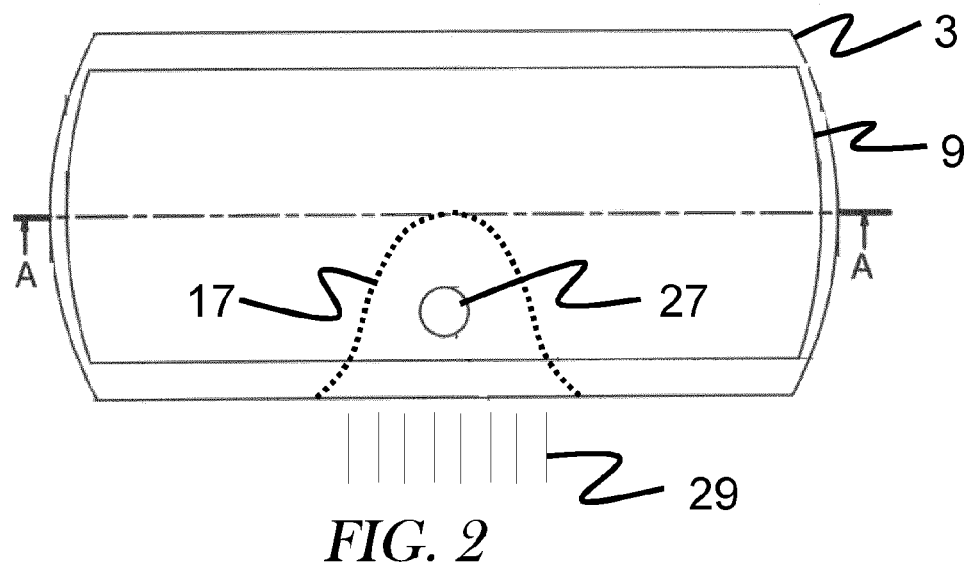
Figure 3:
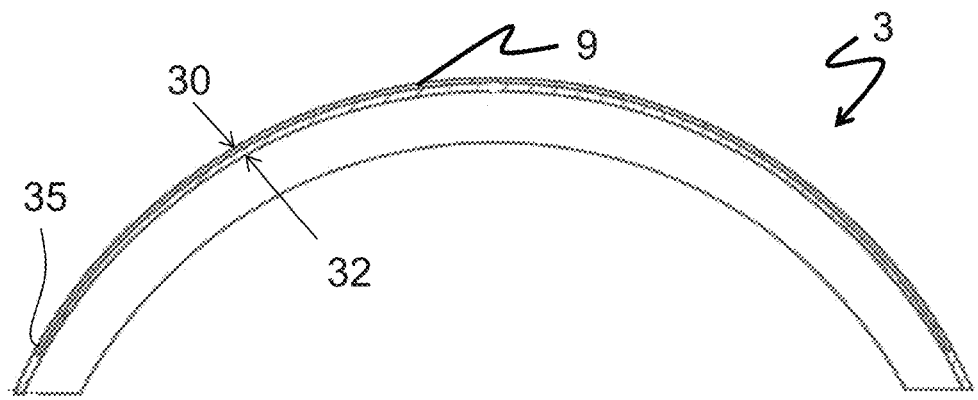
Figure 4:
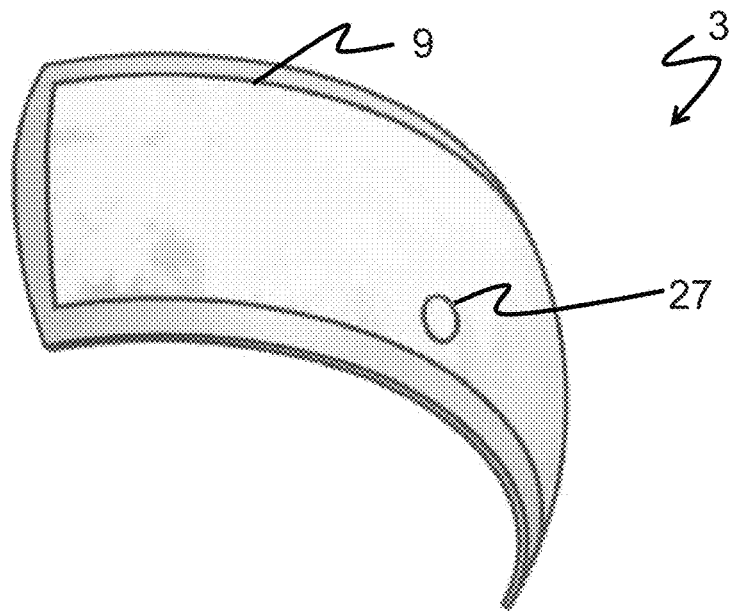

Other features and advantages of the invention will become apparent from reading the following description of one particular nonlimiting embodiment of the invention, in the light of the following figures:

FIG. 1 is a schematic cross section through a mold,
 FIG. 2 is a front-on view of a viewing screen according to the invention,
 FIG. 3 is a cross section through a viewing screen according to FIG. 2, on the line A-A of FIG. 2, and FIG. 4 is a perspective view of a viewing screen according to FIG. 2.

In all the figures, the same elements bear the same reference numerals.

FIG. 1 is a cross section through a mold 1 for the injection molding of a viewing screen 3 (see FIG. 4) with overmolded insert. This mold 1 comprises a concave part 5 and a convex part 7.

As may be seen in FIG. 1, an insert 3 (thick line) is placed in the mold 1. This insert 9 is curved and its dimensions are smaller than the dimensions of the concave form 11 so that the top 13 and bottom 15 edges of the mold (when viewed in the figure) are not in contact with the insert 9. The insert 9 therefore has a size smaller than that of the finished screen (see FIG. 2), and this is advantageous because it saves a not-insignificant surface-area of insert by comparison with the method of the prior art.

The concave part 5 has in its lower part (when viewed in the figure) and which, insofar as the viewing screen is concerned, corresponds to a cutout portion 17 (see FIG. 2) that accommodates the nose of a user, a suction nozzle 21 incorporated into the mold 1 and connected to a vacuum pump 23. When the vacuum pump is operating, the insert 9 is mechanically held against the concave part 5 by suction.

In the embodiment shown, just one suction nozzle is provided, this being located in the zone 17 which, insofar as the viewing screen is concerned, corresponds to the cutout portion that accommodates the nose of the user.

The suction nozzle comprises for example a low-porosity metal insert that prevents injected thermoplastics material from being sucked up and which is incorporated into the concave part 5 of the injection mold 1.

By way of example, the metal, insert has a transverse diameter of between 7.5 mm and 10 mm, preferably 9 mm.

The porosity of the metal insert is below 200 μm, for example between 30 and 100 microns.

The insert 9 may be curved, for example by thermoforming, beforehand before being inserted into the mold, or may be carved by thermoforming once it is in position in the mold and before a thermoplastics material is injected.

The insert 9 is formed for example of three layers (see, e.g., FIG. 3), the intermediate layer 35 being made of polyvinyl alcohol (PVA) polymer and one or both of the outer layer 30, 32 being made up of cellulose triacetate (CTA), polycarbonate (PC) or polyamide (PA). Thus inserts 9 made up of CTA-PVA-CTA, PC-PVA-PC, CTA-PVA-PC, CTA-PVA-PA are envisioned, the first layer 30 of the insert 9 being the layer intended to be furthest away from the eye when the mask is being worn and the third layer 32 being the one intended to be closest to the eye of the user.

In addition, this FIG. 1 shows an injection nozzle 25 for injecting a thermoplastics material such as polycarbonate or polyamide (for example nylon), for example of "crystal" quality, namely that is transparent but untinted, or alternatively that is tinted/colored.

This thermoplastics-material injection nozzle 25 is positioned edge-on in relation to the insert 9, near the suction nozzle 21 and centered with respect to the latter.

The method according to the invention takes place as follows:

An insert 9 that is to be overmolded is placed in the injection mold 1, the insert having been curved beforehand by thermoforming so as to best hug the wall of the concave part of the mold 1.

In order thereafter to hold the insert 9 in the mold 1, the vacuum pump 23 is switched on and generates a vacuum clamping the insert firmly against the wall of the concave part of the mold 1.

By way of example, the suction is between 0.02 and 0.085 MPa.

Next, the convex part 7 of the mold 1 is positioned in relation to the concave part 5 leaving a gap that is to be filled with thermoplastics material and a thermoplastics material such as polycarbonate or polyamide (for example nylon) is injected via the nozzle 25 into the mold 1 to form a mechanical support layer supporting the viewing screen 3.

Finally, the viewing screen 3 thus formed is demolded.

FIG. 2 shows a finished viewing screen 3 that can be used as a mask for example for participating in certain sports such as skiing, for night driving, for a motorcycle helmet, or for protective goggles.

A circle 27 is clearly visible therein and represents the line of the suction nozzle 21. However, this is unimportant because the viewing screen 3 is cut in the part 17 to accommodate the nose of a user.

This FIG. 2 also snows arrows 29 which symbolize the thermoplastics-material injection nozzle 25. It can therefore be seen that this nozzle is centered with respect to the suction nozzle 21.

The advantage of this layout is that the creation of mechanical tension in the insert is reduced, all the tension being concentrated in the zone 17 that will be cut out.

FIG. 3 shows the viewing screen 3 in cross section and FIG. 4 shows it in perspective. The insert 9 can include one or more optical layers such as, for example, the first layer 30, the intermediate layer 35 and the third layer 32.

Of course, the rear face and the front face of the viewing screen may potentially be covered with any coating customarily employed in the field of optical screens in order to afford an additional function.

Nonlimiting examples of the functional coatings that may be applied to one and/or the other face of the screen include coatings that additionally confer impact resistance, confer the functions of antireflective coatings, hard coatings, clean coatings, antifog coatings, antistatic coatings or a combination of some of these functions.

It will therefore be appreciated that the method makes it possible to produce a viewing screen of quality, in particular avoiding impairment of the optical quality of the screen that could result from it being held at several peripheral points and from the resultant surface tensions created upon the injection of the thermoplastics material.

Specifically, the method according to the invention also allows the insert 9 to conform accurately to the shape or cavity of the concave part 5 of the mold 1 and do so without introducing stress. This is important because the thermoforming is not perfectly spherical and at the same radius as the cavity. Thanks to the method of the invention. As a result there is no jerkiness in the flow of hot material during filling which could give rise to visible defects (lines, deformations, etc.) with the insert which without resistance conforms to the shape of the cavity, and this also limits tension.

Of course, the invention is not restricted to the embodiments described but encompasses any variant that falls within the scope of the invention as defined by the claims.

The invention claimed is:

1. A method for producing a viewing screen, the method comprising:

placing a viewing screen insert having first and second opposing surfaces and one or more optical layers between first and second surfaces of an injection mold adapted to receive the viewing screen insert;

applying a vacuum to hold the first surface of the viewing screen insert to the first surface of the injection mold using at least one suction nozzle incorporated into the injection mold, wherein a single one of the at least one suction nozzle is positioned in a zone of the first surface of the injection mold corresponding to a cutout portion of the viewing screen insert configured to accommodate a nose of a user;

injecting a thermoplastics material into the injection mold to form a mechanical support layer supporting the viewing screen insert; and demolding the viewing screen formed from the viewing screen insert and the mechanical support layer.

2. The method as claimed in claim 1, wherein the single suction nozzle positioned in the zone of the first surface of the injection mold corresponding to the cutout portion of the viewing screen insert comprises a low-porosity metal insert preventing the injected thermoplastics material from being sucked up and, wherein the single suction nozzle is incorporated into the first surface of the injection mold.

3. The method as claimed in claim 2, wherein the single suction nozzle has a transverse diameter of between about 7.5 millimeters (mm) and about 10 mm.

4. The method as claimed in claim 2, wherein the metal insert of the single suction nozzle has a porosity of below about 200 micrometers (μm).

5. The method as claimed in claim 1, wherein applying a vacuum to hold the first surface of the viewing screen insert to the first surface of the injection mold using at least one suction nozzle comprises generating a suction through the single suction nozzle between about 0.02 and about 0.085 megapascal (MPa).

6. The method as claimed in claim 1, wherein the viewing screen insert is provided having dimensions smaller than that of the viewing screen.

7. The method as claimed in claim 1, wherein injecting the thermoplastics material into the injection mold to form a mechanical support layer supporting the insert comprises:

positioning an injection nozzle substantially edge-on in relation to the insert, substantially near the suction nozzle and substantially centered relative to the suction nozzle; and injecting the thermoplastics material into the injection mold using the injection nozzle.

8. The method as claimed in claim 1, wherein the thermoplastics material is polycarbonate or polyamide.

9. The method as claimed in claim 1, wherein the insert comprises first, second and third layers having said first and second opposing surfaces, the second layer disposed between the second surface of the first layer and first surface of the third layer, said second layer comprising polyvinyl alcohol (PVA) polymer and one or more of the first and third layers comprising cellulose triacetate, polycarbonate or polyamide.

10. A viewing screen having a front face and a rear face, wherein the front face corresponds to a first surface of the viewing screen and the rear face corresponds to a second opposing surface of the viewing screen, the viewing screen comprising:

a mechanical support layer having first and second opposing surfaces, said mechanical support layer comprising a thermoplastics material, wherein the second surface of the mechanical support layer corresponds to the rear face of the viewing screen; and an insert having first and second opposing surfaces and one or more optical layers, wherein the first surface of the insert corresponds to the front face of the viewing screen, said insert comprising:

an intermediate layer having first and second opposing surfaces, said intermediate layer comprising polyvinyl alcohol polymer; and an outer layer having first and second opposing surfaces, said outer layer comprising a thermoplastics material, wherein the first surface of the outer layer corresponds to the first surface of the insert and the second surface of the outer layer is disposed over the first surface of the intermediate layer, wherein said first surface of the mechanical support layer is disposed over at least the second surface of the insert to produce the viewing screen by injecting the thermoplastics material forming the mechanical support layer into an injection mold adapted to receive the insert, wherein said first surface of the insert is coupled to a first surface of the injection mold during injection of the thermoplastics material using at least one suction nozzle incorporated into the injection mold with a respective one of the at least one suction nozzle positioned in a zone of the first surface of the injection mold corresponding to a cutout portion of the viewing screen configured to accommodate a nose of a user.

* * * * *